US006648920B2

(12) United States Patent
Ferree

(10) Patent No.: US 6,648,920 B2
(45) Date of Patent: Nov. 18, 2003

(54) NATURAL AND SYNTHETIC SUPPLEMENTS TO ENGINEERED ANNULUS AND DISC TISSUES

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/171,260

(22) Filed: Jun. 13, 2002

(65) Prior Publication Data

US 2002/0156533 A1 Oct. 24, 2002

Related U.S. Application Data

(63) Continuation-in-part of application No. 09/688,716, filed on Oct. 16, 2000, now Pat. No. 6,454,804, and a continuation-in-part of application No. 09/638,726, filed on Aug. 14, 2000, now Pat. No. 6,340,369, and a continuation-in-part of application No. 09/415,382, filed on Oct. 8, 1999, now Pat. No. 6,419,704, application No. 10/171,260.
(60) Provisional application No. 60/159,488, filed on Oct. 14, 1999, and provisional application No. 60/371,546, filed on Apr. 10, 2002.

(51) Int. Cl.$^7$ ................................................. A61F 2/44
(52) U.S. Cl. ..................... 623/17.11; 424/93.7; 623/908
(58) Field of Search ........................ 623/17.11–17.16, 623/919, 908, 13.11; 427/93.7; 424/93.7

(56) References Cited

U.S. PATENT DOCUMENTS

| 2,677,369 A | 5/1954 | Knowles ...................... 128/92 |
| 3,366,975 A | 2/1968 | Pangman ........................... 3/36 |
| 3,426,364 A | 2/1969 | Lumb .................................. 3/1 |
| 3,551,560 A | 12/1970 | Thiele ........................... 424/95 |
| 3,593,342 A | 7/1971 | Niebauer ............................ 3/1 |
| 3,648,294 A | 3/1972 | Shahrestani ....................... 3/1 |
| 3,855,638 A | 12/1974 | Pilliar ............................... 3/1 |
| 3,867,728 A | 2/1975 | Stubstad et al. ................... 3/1 |
| 3,875,595 A | 4/1975 | Froning ............................. 3/1 |
| 3,883,902 A | 5/1975 | Lynch ............................. 3/36 |
| 4,229,839 A | 10/1980 | Schwemmer ................. 1/1.91 |
| 4,309,777 A | 1/1982 | Patil .............................. 3/1.91 |
| 4,349,921 A | 9/1982 | Kuntz .............................. 3/1 |
| 4,663,358 A | 5/1987 | Hyon et al. .................... 521/64 |
| 4,707,872 A | 11/1987 | Hessel ........................... 5/451 |
| 4,714,469 A | 12/1987 | Kenna .......................... 623/17 |
| 4,759,766 A | 7/1988 | Buettner-Janz et al. ........ 623/17 |
| 4,772,287 A | 9/1988 | Ray et al. ...................... 623/17 |
| 4,801,299 A | 1/1989 | Brendel et al. ........... 623/16.11 |
| 4,863,477 A | 9/1989 | Monson ........................ 623/17 |
| 4,874,389 A | 10/1989 | Downey ....................... 623/17 |
| 4,904,260 A | 2/1990 | Ray et al. ...................... 623/17 |
| 4,911,718 A | 3/1990 | Lee et al. ...................... 623/17 |
| 4,917,704 A | 4/1990 | Frey et al. .................... 623/17 |
| 4,932,969 A | 6/1990 | Frey et al. .................... 623/17 |
| 4,946,378 A | 8/1990 | Hirayama et al. ............. 623/17 |
| 5,002,576 A | 3/1991 | Fuhrmann et al. ............ 623/17 |
| 5,035,716 A | 7/1991 | Downey ....................... 623/17 |
| 5,047,055 A | 9/1991 | Bao et al. ..................... 623/17 |
| 5,071,437 A | 12/1991 | Steffee, Arthur D. ......... 623/17 |
| 5,108,438 A | 4/1992 | Stone ........................... 623/17 |
| 5,123,926 A | 6/1992 | Pisharodi ..................... 623/17 |
| 5,171,280 A | 12/1992 | Baumgartner ................ 623/17 |
| 5,171,281 A | 12/1992 | Parsons et al. ................ 623/17 |
| 5,192,326 A | 3/1993 | Bao et al. ..................... 623/17 |
| 5,246,458 A | 9/1993 | Graham ........................ 623/17 |
| 5,258,031 A | 11/1993 | Salib et al. ................... 623/17 |
| 5,258,043 A | 11/1993 | Stone ........................... 623/66 |
| 5,314,477 A | 5/1994 | Marnay ........................ 623/17 |
| 5,320,644 A | 6/1994 | Baumgartner ................ 623/17 |
| 5,370,697 A | 12/1994 | Baumgartner ................ 623/17 |
| 5,375,823 A | 12/1994 | Navas .......................... 267/195 |
| 5,401,269 A | 3/1995 | Buttner-Janz et al. ........ 623/17 |
| 5,425,773 A | 6/1995 | Boyd et al. ................... 623/17 |
| 5,458,642 A | 10/1995 | Beer et al. .................... 623/17 |
| 5,464,439 A | 11/1995 | Gendler .................... 623/16.11 |
| 5,514,180 A | 5/1996 | Heggeness et al. ........ 623/17.11 |
| 5,534,028 A | 7/1996 | Bao et al. ..................... 623/17 |
| 5,534,030 A | 7/1996 | Navarro et al. ............... 623/17 |
| 5,545,229 A | 8/1996 | Parsons et al. ............... 623/17 |
| 5,556,431 A | 9/1996 | Buttner-Janz ................ 623/17 |
| 5,609,635 A | 3/1997 | Michelson .................... 623/17 |
| 5,645,596 A | 7/1997 | Kim et al. ..................... 623/17 |
| 5,645,597 A | 7/1997 | Krapiva ........................ 623/17 |
| 5,674,294 A | 10/1997 | Bainville et al. ............. 623/17 |

(List continued on next page.)

OTHER PUBLICATIONS

North American Spine Society 13 Annual Meeting, San Francisco Hilton and Towers. Oct. 28–31, 1998; Barron Lonner Md., Et al., "Tissue Engineered Regeneration of the Intervertebral Disc".
Orthopedics Today, Jul. 2000.
"Proceedings 14th Annual Meeting" North American Spine Society, Oct. 1999.
"Proceedings 13th annual Meeting" North American Spine Society, Oct. 1998.
Steven Frick MD, Spine vol. 19, No. 16, pp. 1826–1835, 1994.

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Fibrocytes, annulus fibrosis cells, cells that differentiate into annulus fibrosis cells, or cells that function like annulus fibrosis cells are harvested and combined with the extracellular matrix of the annulus fibrosis from a recently deceased human or animal to produce an engineered annulus fibrosis. Any suitable material(s) are then added to the engineered disc tissue to restore disc height. For example, a shape-memory material or alloy that changes shape from a long narrow shape to a spherical shape would facilitate insertion through a relatively small incision followed by useful height restoration. Additional therapeutic substances like culture medium, growth factors, differentiation factors, hydrogels, polymers, antibiotics, anti-inflammatory medications, or immunosuppressive medications could be added to the transplanted annulus fibrosis tissue. The process can be used to replace or repair other tissues or organs of the body such as the meniscus of the knee.

9 Claims, No Drawings

U.S. PATENT DOCUMENTS

| | | |
|---|---|---|
| 5,674,296 A | 10/1997 | Bryan et al. .................. 623/17 |
| 5,683,465 A | 11/1997 | Shinn et al. .................. 623/17 |
| 5,702,450 A | 12/1997 | Bisserie ....................... 623/17 |
| 5,711,960 A | 1/1998 | Shikinami .................. 424/426 |
| 5,716,416 A | 2/1998 | Lin ............................. 623/17 |
| 5,800,549 A | 9/1998 | Bao et al. ..................... 623/17 |
| 5,824,093 A | 10/1998 | Ray et al. ..................... 623/17 |
| 5,824,094 A | 10/1998 | Serhan et al. ................. 623/17 |
| 5,865,845 A | 2/1999 | Thalgott ....................... 623/17 |
| 5,865,846 A | 2/1999 | Bryan et al. .................. 623/17 |
| 5,888,226 A | 3/1999 | Rogozinski .................. 623/17 |
| 5,893,889 A | 4/1999 | Harrington ................... 623/17 |
| 5,899,941 A | 5/1999 | Nishijima et al. ............ 623/17 |
| 5,928,284 A | 7/1999 | Mehdizadh ................... 623/17 |
| 5,964,807 A | 10/1999 | Gan et al. ................. 623/17.11 |
| 5,976,186 A | 11/1999 | Bao et al. ................. 623/17.16 |
| 6,022,376 A | 2/2000 | Assell et al. ............. 623/17.16 |
| 6,090,112 A | 7/2000 | Zucherman et al. .......... 606/61 |
| 6,110,210 A | 8/2000 | Norton et al. ........... 623/17.16 |
| 6,113,639 A | 9/2000 | Ray et al. ................ 623/17.16 |
| 6,132,465 A | 10/2000 | Ray et al. ................ 623/17.16 |
| 6,146,420 A | 11/2000 | McKay .................... 623/17.11 |
| 6,187,048 B1 * | 2/2001 | Milner et al. ............ 623/17.12 |
| 6,231,615 B1 | 5/2001 | Preissman ................ 623/23.73 |
| 6,245,107 B1 | 6/2001 | Ferree .................... 623/17.11 |
| 6,332,779 B1 | 12/2001 | Boyce et al. ................ 433/215 |
| 6,340,369 B1 * | 1/2002 | Ferree .................... 623/17.11 |
| 6,344,058 B1 * | 2/2002 | Ferree .................... 623/17.11 |
| 6,352,557 B1 * | 3/2002 | Ferree .................... 623/17.11 |
| 6,402,784 B1 * | 6/2002 | Wardlaw ................. 623/17.11 |
| 6,419,702 B1 * | 7/2002 | Ferree .................... 623/17.11 |
| 6,419,704 B1 * | 7/2002 | Ferree .................... 623/17.12 |
| 6,454,804 B1 * | 9/2002 | Ferree .................... 623/17.11 |
| 6,592,625 B2 * | 7/2003 | Cauthen ................. 623/17.16 |

\* cited by examiner

NATURAL AND SYNTHETIC SUPPLEMENTS TO ENGINEERED ANNULUS AND DISC TISSUES

REFERENCE TO RELATED APPLICATIONS

This application is a continuation-in-part of U.S. patent application Ser. No. 09/688,716, filed Oct. 16, 2000 now U.S. Pat. No. 6,454,804, which claims priority from U.S. Provisional Patent Application Serial No. 60/159,488, filed Oct. 14, 1999, and is a continuation-in-part of U.S. Patent Application Ser. Nos. 09/638,726, filed Aug. 14, 2000, now U.S. Pat. No. 6,340,369, and 09/415,382, filed Oct. 8, 1999 now U.S. Pat. No. 6,419,704. This application also claims priority from U.S. Provisional Patent Application Serial No. 60/371,546, filed Apr. 10, 2002; the entire content of each application and issued patent being incorporated herein by reference.

FIELD OF THE INVENTION

This invention relates generally to the treatment of diseased or traumatized intervertebral discs, and more particularly, to the use of engineered tissues in conjunction with such treatments.

BACKGROUND OF THE INVENTION

Intervertebral discs provide mobility and a cushion between the vertebrae. At the center of the disc is the nucleus pulposus. The nucleus pulposus is surrounded by the annulus fibrosis, which is comprised of cells (fibrocyte-like and chondrocyte-like), collagen fibers, and non-fibrillar extracellular matrix. The components of the annulus are arranged in 15–25 lamellae around the nucleus pulposus. The fibers in the lamellae alternate their direction of orientation by 30 degrees between each band.

The annulus fibrosis has three important functions. First, the annulus contains the nucleus pulposus. Second, the annulus fibrosis, with other ligaments, connects the vertebrae of the spine. Lastly, the annulus fibrosis helps to control movement between the vertebrae.

The fibers of the annulus can tear causing pain and possible extrusion of the nucleus pulposus. Extrusion of the nucleus pulposus is known as a disc herniation. Disc herniations can compress nerves or the spinal cord resulting in arm or leg pain and dysfunction. Surgery to repair disc herniations leaves a hole in the annulus fibrosis. The hole in the annulus acts as a pathway for additional material to protrude into a nerve, resulting in a recurrence of the herniation. My U.S. Pat. No. 6,245,107 and Patent Cooperation Treaty Application Serial No. PCT/US/14708 describe methods and devices to occlude annular defects.

To date, the treatment of tears or defects of the annulus fibrosis has relied for the most part on eliminating the defective disc or disc function. This may be accomplished by fusing the vertebra on either side of the disc.

In terms of replacement, prior-art techniques replace either the nucleus or the nucleus and annulus functions. This may be accomplished using natural or synthetic materials, or a combination of natural and artificial components. Although transplantation of living cells risks rejection by graft host reaction, certain of my previous disclosures, including those in U.S. patent application Ser. Nos. 09/688,716 and 09/638,726 (now U.S. Pat. No. 6,340,369) recognize that transplantation of the extracellular matrix of the annulus fibrosis is unlikely to incite graft host reaction. As such, fibrocytes are harvested, cultured, then added to annulus fibrosis extracellular matrix obtained from recently deceased humans or animals. The combined annulus fibrosis is then introduced into the injured or diseased disc.

The cells or engineered tissues may be introduced using any surgical technique, including percutaneous or laparoscopic approaches. As one delivery mechanism, a passageway may be formed through the annulus fibrosis, with the cells or engineered disc tissue being introduced into the disc through the passageway. In particular, the engineered disc tissue may be sewn or otherwise adhered to the inside or outside of the existing annulus fibrosis using a surgical procedure performed from the posterior or anterior portion of the body.

SUMMARY OF THE INVENTION

Certain of my co-pending patent applications and issued patents referenced above disclose the step of adding one or more substances to disc-related cells or annular tissue prior to transplantation. Such substances could include culture media, growth factors, differentiation factors, hydrogels, polymers, antibiotics, anti-inflammatory medications, immuno-suppressive medications, or any useful combination thereof. These previous disclosures further teach that such substances and materials may be combined with any compatible nucleus replacement procedure, including the embodiments described in co-pending U.S. Pat. No. 6,371,990 and the continuations thereof, all of which are incorporated herein by reference.

According to this invention, fibrocytes, annulus fibrosis cells, cells that differentiate into annulus fibrosis cells, or cells that function like annulus fibrosis cells are harvested and combined with the extracellular matrix of the annulus fibrosis from a recently deceased human or animal to produce an engineered annulus fibrosis. In the event that the engineered disc tissue alone is not sufficiently strong to restore the height of the degenerated disc, any suitable material may be added to the engineered disc tissue to restore disc height.

According to one preferred embodiment, a disc augmentation device incorporating a shape-memory material is used to restore disk height as it changes shape. For example, a shape-memory material or alloy that changes shape from a long narrow shape to a spherical shape would facilitate insertion through a relatively small incision followed by useful height restoration, as disclosed in my U.S. Provisional Patent Application Serial No. 60/371,546, filed Apr. 10, 2002, the entire content of which is incorporated herein by reference. Such a composite engineered system could provide long-term disc function, eventually hold the disc height after the synthetic material provides the force needed to restore disc height.

DETAILED DESCRIPTION OF THE INVENTION

Broadly according to the inventions disclosed in U.S. patent application Ser. Nos. 09/688,716 and 09/638,726 (now U.S. Pat. No. 6,340,369), fibrocytes are harvested, cultured, added to annulus fibrosis extracellular matrix material, then sewn or otherwise placed relative to an injured or diseased disc. The annulus fibrosis cells and extracellular matrix are preferably harvested from a live human, though recently deceased human or animal donors may alternatively be used. Depending upon the extent of the harvest, the recipient may function at least in part as a donor, or the tissues from others, including fetal or embryo sources, may be used.

The fibrocytes may be obtained from a tendon of the patient; for example, a palmaris longus tendon may be removed from one arm. The harvested fibrocytes are isolated and cultured using standard techniques. Precursor cells of the annulus fibrosis, annulus fibrosis cells, chondrocytes, or other living cells that could function like annulus fibrosis cells or that could differentiate into cells to build a functional annulus fibrosis may also be used. The cells from the culture are then implanted into the donor extracellular matrix to form a living annulus fibrosis. In the preferred embodiment, the cells are injected into small holes drilled into the donor extracellular matrix.

The engineered tissue may be added to the inside or the outside of the patient's annulus. Surgical procedures to access the inner or outer surface of the annulus fibrosis are well known to those skilled in the art. For example, the engineered annulus could be sutured, placed against, or "glued" to the patient's annulus. Platelet rich plasma combined with calcium and thrombin or "fibrin glue" could be used to glue the annular tissues together.

Additional substances may also be added to the transplanted annulus. For example, resorbable culture medium, tissue growth or differentiation factors (recombinant generated morphogenetic proteins, PDGF, TGF-β, EGF/TGF-α, IGF-I, βFGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be used.

In an alternative embodiment, living cells are not added to the harvested annulus fibrosis. The harvested annulus fibrosis is processed as described above to kill the living host annulus cells.

Although annulus fibrosis augmentation and/or transplantation is being described herein in detail, the invention is not limited to treatment of the intervertebral disc. For example, the invention could also be used to treat other tissues of the body such as the meniscus of the knee. In such cases, a meniscus would be removed from recently deceased humans. The harvested meniscus would be processed to kill the cells but preserve the extracellular matrix. Fibroctyes harvested as described above would then be added to the extracellular matrix prior to insertion of the engineered meniscus into a patient's knee. Similarly, chondrocytes could be harvested and added to the meniscus extracellular matrix as described in my pending U.S. patent Ser. Nos. 09/639,309, 09/628,727, 09/638,726, and 09/638,242, all of which are incorporated herein by reference.

Similarly, the process could be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

In the event that the engineered disc tissue alone is not sufficiently strong to restore the height of the degenerated disc, any suitable material may be added to the engineered disc tissue to restore disc height. For example, a disc augmentation device incorporating a shape-memory material could be used to restore disk height as it changes shape. A shape-memory material or alloy that changes shape from a long narrow shape to a spherical shape would facilitate insertion through a relatively small incision followed by useful height restoration, as disclosed in my U.S. Provisional Patent Application Serial No. 60/371,546, filed Apr. 10, 2002, the entire content of which is incorporated herein by reference. Such a composite engineered system could provide long-term disc function, eventually hold the disc height after the synthetic material provides the force needed to restore disc height.

I claim:

1. A method of augmenting the annulus fibrosis of an intervertebral disc having a disc height, the method comprising the steps of:

harvesting fibrocytes, annulus fibrosis cells, cells that differentiate into annulus fibrosis cells, or cells that function like annulus fibrosis cells;

harvesting the extracellular matrix of the annulus fibrosis from a recently deceased human or animal;

combining the harvested cells with the extracellular matrix to produce an engineered annulus fibrosis;

adding at least one disc-height restorative material to the combined cells and matrix thus forming an engineered annulus fibrosis; and transplanting the engineered annulus fibrosis into or onto the disc.

2. The method of claim 1, further including the steps of:

forming a passageway through the disc and transplanting the engineered annulus into the disc through the passageway, or placing the engineered annulus onto the disc.

3. The method of claim 1, further including the step of adding one or more therapeutic substances to the engineered annulus fibrosis.

4. The method of claim 3, wherein the therapeutic substances include one or more of the following:

culture media, growth factors, differentiation factors, hydrogels, polymers, antibiotics, anti-inflammatory medications, or immunosuppressive medications.

5. The method of claim 1, further including the step of keeping the harvested cells viable until placed into the disc being treated.

6. The method of claim 1, wherein the disc-height restorative material is a shape-memory material.

7. An engineered annulus fibrosis according to the method of claim 1.

8. The engineered annulus fibrosis of claim 1, further including one or more therapeutic substances.

9. The engineered annulus fibrosis of claim 8, wherein the therapeutic substances include one or more of the following:

culture media, growth factors, differentiation factors, hydrogels, polymers, antibiotics, anti-inflammatory medications, or immunosuppressive medications.

* * * * *